United States Patent [19]

Moreschini et al.

[11] Patent Number: 4,499,302

[45] Date of Patent: Feb. 12, 1985

[54] PROCESS FOR THE PRODUCTION OF METHACRYLIC ACID

[75] Inventors: Luciano Moreschini, Pordenone; Leonardo Dalloro, Bollate; Enrico Cavaterra, Milan; Guido Petrini, Milan; Romano Covini, Milan, all of Italy

[73] Assignee: Montedison S.p.A., Milan, Italy

[21] Appl. No.: 120,397

[22] Filed: Feb. 11, 1980

[51] Int. Cl.$^3$ .................... C07C 51/377; C07C 57/05
[52] U.S. Cl. .................. 562/599; 260/405.5; 502/213; 568/397; 585/638
[58] Field of Search .............. 562/599; 260/405.5; 252/435, 437

[56] References Cited

U.S. PATENT DOCUMENTS 3,398,100  8/1968  Christmann ............... 252/435
3,855,279  12/1974 Watkins ................... 562/599
3,948,959  4/1976  Cavaterra et al. .......... 562/599
3,993,591  11/1976 Cichowski et al. .......... 252/432
4,029,695  6/1977  Watkins ................... 562/599
4,232,174  11/1980 Statz et al. ............... 562/599

Primary Examiner—Vivian Garner
Attorney, Agent, or Firm—Stevens, Davis, Miller & Mosher

[57] ABSTRACT

Preparation of aliphatic alpha, beta-unsaturated carboxylic acids from the corresponding saturated acids by oxidative dehydrogenation, at a temperature between 250° and 500° C., in the presence of a catalyst of empirical formula: $FeP_xMe_yMe'_tO_z$ wherein Me is at least one alkali or alkaline earth element, Me' is at least one element selected from the group consisting of Ni, Cu, Ce, Al, Zr, Hf and Pr, x is between 0.2 and 15, y is between 0.01 and 2, t is between 0.01 and 5 and z is such as to satisfy the valencies of the other elements.

1 Claim, No Drawings

PROCESS FOR THE PRODUCTION OF METHACRYLIC ACID

BACKGROUND OF THE INVENTION

Aliphatic alpha, beta-unsaturated acids have been already obtained from the corresponding saturated acids by a dehydrogenation in the presence of oxygen on solid catalysts; such catalysts, according to the French Pat. No. 2,135,786, are for instance mixed phosphates of iron and bismuth. Still another patent (U.S. Pat. No. 3,948,959) relates to the use of mixed phosphates of iron and alkali or alkaline earth elements.

DISCLOSURE OF THE INVENTION

In its more general form, the invention concerns a process for the production of aliphatic alpha, beta-unsaturated carboxylic acids having from 3 to 8 carbon atoms, by means of an oxidative dehydrogenation at a temperature from 250° to 500° C., of the corresponding saturated acids. The process is characterized in that the catalyst consists of a compound of the empirical formula:

$$FeP_xMe_yMe'_tO_z$$

wherein Me represents at least one alkali or alkaline earth element, Me' represents at least one element selected from the group consisting of nickel, copper, cerium, aluminum, praseodinium, hafnium and zirconium, x is between 0.2 and 15, y is between 0.01 and 2, t is between 0.01 and 5 and z is such as to satisfy the valencies of the other elements.

There are different possible ways for carrying out the invention; more particularly it will be remarked that the process may be realized in a continuous or discontinuous way. The saturated acid may be fed into the catalytic reactor in admixture with oxygen or air, or with one or more diluents such as nitrogen, steam, $CO_2$, etc. The quantity of aliphatic acid in the reacting mixture, in general, is between 1% and 40% by volume, while the molar ratio oxygen/saturated acid must be, in general, between 0.1/1 and 10/1, but preferably between 0.4/1 and 4/1.

As starting saturated acids may be used with advantageous results isobutyric acid and propionic acid for obtaining respectively methacrylic and acrylic acid.

The catalytic composition may be used without a carrier and as such it develops an excellent catalytic activity. In case one should prefer to use it in combination with a carrier, as such may be used any material suitable for the purpose, such as for instance: silica alumina, silicon carbide, silica-alumina, silicates, borates, carbonates, provided they are stable under the reaction conditions to which they will be subjected. The quantity of active catalytic compositions, with respect to the weight of the carrier, may vary within a wide range depending on the characteristics of the carrier itself and on the method used for its preparation.

The process may be used by employing the catalyst in the form of either a fixed or a fluidized bed, in this latter case the nature of the carrier and the method of preparation for obtaining a microspheroidal catalyst with a suitable granulometric distribution assume a particular importance. A microspheroidal catalyst may be obtained by various techniques. For instance, by spray-drying a solution or suspension of the carrier and of the components of the active catalytic composition, or by impregnation of a preformed microspheroidal carrier with a solution of the components of the catalytically active composition.

As starting compounds for the preparation of the catalytic composition according to this invention, for instance may be used the following compounds of alkaline metal: nitrates, oxides, hydroxides, carbonates, bicarbonates, nitrites, phosphates, silicates, and the salts of oxyacids, or mono- or polycarboxylic organic acids such as formates, oxalates, citrates, tartrates, etc.

The iron-, copper-, nickel- and cerium-compounds may be chosen, depending on the method used, from amongst nitrates, chlorides, sulphates, carbonates, salts of organic mono-or polycarboxylic acids, chelates, etc.

Zirconium compounds may be selected from the group comprising nitrate, chloride, sulphate, zirconyl compounds and so on and praseodinium compounds may be selected from the group comprising nitrate, oxides, sulphate, chloride, carbonate, salts of organic mono-or poly-carboxylic acids, chelates and so on.

The starting aluminum compounds may be chosen, depending on the method used, from amongst nitrate, sulphate, salts of organic mono- or polycarboxylic acids or chelates. For alkali and alkaline earth metals may be used: chlorides, sulphates, carbonates, salts of organic mono- or poly-carboxylic acids, etc., while for the phosphorus may be used alkaline phosphates, ammonium phosphates, phosphoric and phosphorous acids, etc.

All preparation methods involve a final phase of activation of the catalytic composition, consisting in a heating of the composition in the presence of air or of a mixture of air and steam (water vapor), at a temperature between 400° and 700° C. The preparation of the catalyst may be carried out according to the known methods of the technique of the field. In the following will be given a few methods by way of examples:

(1) To an aqueous solution of phosphoric acid was added a compound of element Me; the mixture thus obtained was thereupon slightly heated (to 40°–50° C.) and then was additioned with the iron compound and compounds of element Me'. The mixture thus obtained was then slowly treated under stirring, with 32% ammonia, until reaching a pH value of 6 or 7; it was then slowly brought to dryness under constant stirring and the residue was dried overnight at 130° C. and then activated in the air at 540° C. for 2 hours. The calcined mass was thereupon ground and screened; the fraction between 20 and 35 mesh is suitable for the use in a fixed bed reactor.

(2) A suitable mixture of metal compounds is digested with water and phosphoric acid and then brought slowly to dryness under constant stirring. The residue is then finely ground and then dried at 130° C., overnight. The mass thus obtained is then activated at 600° C. in the air for 2 hours.

(3) The residue of method 1, dried at 130° C., is treated at 300° C. in the air. The mass is then ground to below 25 mesh; additioned with 10% of powdery stearic acid, it is then formed into pellets 4×4 mm. The pellets thus obtained are then activated for 2 hours in the air at 540° C.

(4) A suitable solution of the catalyst components, having a volume corresponding to that of the carrier, was used for impregnating a commercial microspheroidal silica. The mass thus obtained is allowed to rest for 2 or 3 hours, after which it is brought to dryness under stirring and then further dried at 130° C. overnight. The product thus obtained is then activated in a fluidized bed in the air for 2 hours at 550° C. This same method of preparation is also suitable for preparing catalysts for fixed beds, by using a suitable carrier.

The use of the catalysts hereinabove allows one to obtain high yields in unsaturated acid and very high conversions of the corresponding saturated acid without the necessity of carrying out a strong dilution of the reactants with inert gases such as nitrogen. These results may be ascribed to the fact that the catalysts according to this invention promote an oxidative dehydrogenation process of regular running and which is easily controllable as far as the reaction temperature and the contact times are concerned.

The reactants may be fed in on the catalyst, already either completely or partially pre-mixed, or altogether separately. The feeding of the reactants either separately or partially pre-mixed, in general may be more conveniently applied to a fluid-bed reactor. It is also possible to feed part of the air or, if desired, also the whole or a part of the saturated acid into the lower part of the reactor and feed then in one or more upper points inside the catalytic bed the remaining quantities of reactants.

When the reaction is performed within a fixed bed, the catalyst can be placed inside of the pipes of a tube bundle, while removing the reaction heat by means of suitable fluids circulating on the outside of the tubes and, for instance more commonly, by means of mixtures of molten salts. One may also operate in a reactor consisting of a plurality of adiabatic reaction stages alternated by cooling zones for the cooling of the reacted mixture.

The reaction is carried out at a temperature between 250° C. and 500° C., but preferably between 340° and 440° C. The residence time, expressed in seconds as a ratio between the volume of the catalytic bed and the volumes per second of gaseous mixture of reactants fed in, measured under average temperature and pressure conditions existing in the catalytic bed, may vary depending on the nature of the catalytic bed, fixed or fluidized, and on the granulometric size of the catalyst. In general it may be between 0.1 and 20 seconds; a preferred time range, corresponding to the most common, practical operational conditions, goes from 0.3 to 15 seconds. The total pressure under which the reaction is performed is not particularly critical and may, thus, vary within a wide range; it is however partly dictated by economical considerations: in general, one operates, thus, at pressures near atmospheric pressure and more precisely at slightly higher then atmospheric pressure.

The following examples are given with the purpose of further illustrating the invention without, however, limiting the same in scope.

EXAMPLE 1

The catalyst was prepared according to the above described Method 1, and more particularly, there were dissolved 303.3 g of iron nitrate, 50.5 g of potassium nitrate, 145.5 g of nickel nitrate and 222 g of an 85% aqueous phosphoric acid in 600 cm³ of water. This solution was then slowly treated, under stirring, with 440 cm³ of 32% aqueous ammonia. The slurry thus obtained was then slowly brought to dryness under constant stirring and then was further dried for 12 hours at 130° C. The product thus obtained was then activated in a muffle for 2 hours at 540° C. The atomic ratios of the elements in the catalyst were represented by the empirical formula:

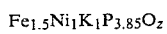

$Fe_{1.5}Ni_1K_1P_{3.85}O_z$

The oxidative dehydrogenation reaction was carried out in a fixed bed reactor and the fed-in mixture consisted of isobutyric acid, air and water in the following molar ratios: 1:3:28. The reaction temperature amounted to 392° C. while the residence time was 0.3 seconds. On the basis of a gas-chromatographic analysis of the reaction gases, there was calculated a yield in methacrylic acid of 61.3%, meaning for yield the ratio:

$$r = \frac{\text{g of carbon of the obtained methacrylic acid}}{\text{g of carbon of the fed in isobutyric acid}} \times 100$$

Data and results are tabulated in Table I; in said table the following definitions of selectivity (s) and conversion (c) are applicable:

$$s = \frac{\text{g of carbon of the obtained methacrylic acid}}{\text{g of carbon of transformed isobutyric acid}} \times 100$$

$$c = \frac{\text{g of carbon in the transformed isobutyric acid}}{\text{g of carbon in the fed in isobutyric acid}} \times 100$$

from a short calculation it turns out that $r = c \times s \times 10^{-2}$.

EXAMPLE 2

Example 1 was repeated, but lowering the temperature of the reaction down to 365° C. and by bringing the residence time to 1 second. Data and results have been tabulated in Table I.

EXAMPLE 3

Example 1 was repeated, but feeding in isobutyric acid, air and water in molar ratios of 1:2:28, and by lowering the temperature of reaction to 375° C. and bringing the residence time to 1.0 seconds. Data and results obtained have been recorded in Table I.

EXAMPLE 4

The catalyst was prepared according to the above described method 1, varying however the atomic ratios of the elements in such a way as to get a product of the empirical formula:

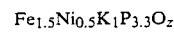

$Fe_{1.5}Ni_{0.5}K_1P_{3.3}O_z$

It was then proceeded as in example 1, bringing the temperature up to 390° C. and the residence time to 1.0 seconds. Data and results have been recorded in Table I.

EXAMPLE 5

The catalyst has been prepared according to the above described method 1, varying the atomic ratios of the elements in such a way as to get a compound of the empirical formula:

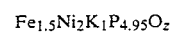

$Fe_{1.5}Ni_2K_1P_{4.95}O_z$

Thereupon it was proceeded as in example 1, lowering the temperature to 360° C. and bringing the residence time to 1.0 seconds. Data and results obtained have been recorded in Table I.

EXAMPLE 6

The catalyst was prepared according to example 1, replacing however nickel by copper so as to obtain a product having the empirical formula:

$$Fe_{1.5}Cu_1K_1P_{3.85}O_z$$

It was then proceeded as in example 1, bringing the temperature to 390° C. and the residence time up to 3.0 seconds. Data and results have been recorded in Table I.

EXAMPLE 7

The catalyst was prepared as in example 6, by varying the atomic ratios of the elements so as to obtain a compound having the empirical formula:

$$Fe_{1.5}Cu_{0.5}K_1P_{3.3}O_z$$

Thereupon it was proceeded as in example 3, bringing the reaction temperature up to 410° C. and the residence time down to 0.5 seconds. Data and results have been recorded in Table I.

EXAMPLE 8

The catalyst was prepared according to example 1, replacing nickel by cerium, so as to obtain a compound of empirical formula:

$$Fe_{1.5}Ce_1K_1P_{3.85}O_z$$

The oxidative dehydrogenation reaction was carried out in a reactor loaded with the above catalyst, in the form of a fixed bed.

The fed-in mixture consisted of isobutyric acid, air and water in molar ratios of 1:4:28, the reaction temperature was 362° C. while the residence time was 0.5 seconds. Data and results have been recorded in Table I.

EXAMPLE 9

The catalyst was prepared as in example 8, varying the atomic ratios of the elements so as to get a compound of the empirical formula:

$$Fe_{1.5}Ce_{0.5}K_1P_{3.3}O_z$$

Thereupon the procedure was as in example 1, bringing the temperature of the reaction to 375° C. and the residence time to 1.0 seconds. The results have been recorded in Table I.

EXAMPLE 10

The catalyst was prepared according to example 8, varying the atomic ratios of the elements in such a way as to get a compound of empirical formula:

$$Fe_{1.5}Ce_2K_1P_{4.95}O_z$$

Thereupon the procedure was as in example 1, bringing the reaction temperature to 360° C. and the contact time to 0.5 seconds. Data and results have been recorded in Table I.

EXAMPLE 11

The catalyst was prepared as in example 1, replacing nickel by zirconium so as to get a compound of empirical formula:

$$Fe_{1.5}Zr_1K_1P_{3.85}O_z$$

The oxidative dehydrogenation reaction was carried out in a reactor loaded with the above catalyst, in the form of a fixed bed. The fed-in mixture consisted of isobutyric acid, air an water in molar ratios 1:2.5:28. The reaction temperature amounted to 410° C. and the residence time was 0.3 seconds. Data and results have been recorded in Table I.

EXAMPLE 12

Example 11 was repeated, except that the fed-in mixture consisted of isobutyric acid, air and water in a molar ratio of 1:2:28, while the temperature amounted to 430° C. and the residence time to 0.3 seconds. Data and results have been recorded in Table I.

EXAMPLE 13

The catalyst was prepared as in example 11, replacing zirconium by praseodinium, so as to obtain a compound of the empirical formula:

$$Fe_{1.5}Pr_1K_1P_{3.85}O_z$$

The procedure was as as in example 11, bringing the reaction temperature to 390° C. and the residence time to 0.3 seconds. Data and results have been recorded in Table I.

EXAMPLE 14

The catalyst was prepared according to example 11, replacing zirconium by aluminum and varying the atomic ratios of the elements so as to get a compound of the empirical formula:

$$Fe_{1.5}Al_1K_1P_{3.65}O_z$$

Thereupon the procedure was as in example 11, bringing the reaction temperature to 360° C. and the residence time to 1 second. Data and results have been recorded in Table I.

EXAMPLE 15

Example 14 was repeated, but the fed-in mixture consisted of isobutyric acid, air and water in molar ratios equal to 1:3:28. The reaction temperature was brought to 390° C. while the residence time was 1.0 second. Data and results have been recorded in Table I.

EXAMPLE 16

The catalyst was prepared according to example 1, replacing potassium by calcium so as to get a compound of empirical formula:

$$Fe_{1.5}Ca_1Ni_1P_{3.85}O_z$$

Thereupon the procedure was as in example 1, bringing the reaction temperature to 375° C. and the residence time to 1.0 second. Data and results have been recorded in Table I.

EXAMPLE 17

Example 16 was repeated, but the fed in mixture consisted of isobutyric acid, air and water in molar ratios of 1:4:28. The reaction temperature was 360° C. while the residence time amounted to 0.5 seconds. Data and results have been recorded in Table I.

TABLE I

| Example n° | Me'$_t$Me P$_x$ (Fe = 1.5; O = z) | (CH$_3$)$_2$CHCOOH air:H$_2$O | T °C. | Time (sec.) | Conversion (%) | Selectivity methacrylic acid | Other selectivities propylene | Acetone | CO$_2$ | CO | Yield (%) | Yield time |
|---|---|---|---|---|---|---|---|---|---|---|---|---|
| 1 | NiKP$_{3.85}$ | 1:3:28 | 392 | 0.3 | — | — | — | — | — | — | 61.3 | 204 |
| 2 | NiKP$_{3.85}$ | 1:3:28 | 365 | 1 | 88.4 | 77.8 | 3.0 | 13.0 | 5.0 | 1.3 | 68.8 | 68.8 |
| 3 | NiKP$_{3.85}$ | 1:2:28 | 375 | 1 | 79.9 | 80.7 | 3.5 | 11.1 | 3.3 | 1.4 | 64.5 | 64.5 |
| 4 | Ni$_{0.5}$KP$_{3.4}$ | 1:3:28 | 390 | 1 | 92.4 | 74.5 | 4.7 | 14.2 | 4.4 | 2.3 | 68.6 | 68.8 |
| 5 | Ni$_2$KP$_{4.95}$ | 1:3:28 | 360 | 1 | 81.6 | 74.0 | 3.2 | 16.1 | 5.8 | 0.9 | 60.4 | 60.4 |
| 6 | CuKP$_{3.85}$ | 1:3:28 | 390 | 3 | 93.0 | 71.5 | 4.4 | 16.4 | 4.5 | 3.2 | 66.5 | 22.2 |
| 7 | Cu$_{0.5}$KP$_{3.3}$ | 1:2:28 | 410 | 0.5 | 84.4 | 75.5 | 7.1 | 12.0 | 3.0 | 2.4 | 63.7 | 127.4 |
| 8 | CeKP$_{3.85}$ | 1:4:28 | 362 | 0.5 | 78.8 | 73.4 | 2.2 | 17.4 | 5.7 | 1.3 | 57.8 | 105.6 |
| 9 | Ce$_{0.5}$KP$_{3.3}$ | 1:3:28 | 375 | 1 | — | — | — | — | — | — | 73 | 73 |
| 10 | Ce$_2$KP$_{4.95}$ | 1:3:28 | 360 | 0.5 | 84.4 | 77.6 | 3.2 | 14.1 | 3.0 | 2.1 | 65.5 | 131.0 |
| 11 | ZrKP$_{3.85}$ | 1:2.5:28 | 410 | 0.3 | — | — | — | — | — | — | 76.5 | 255.0 |
| 12 | ZrKP$_{3.85}$ | 1:2:28 | 430 | 0.3 | 79.4 | 79.5 | 7.0 | 9.1 | 2.7 | 1.7 | 63.1 | 210.3 |
| 13 | PrKP$_{3.85}$ | 1:2.5:28 | 390 | 0.3 | 89.1 | 78.4 | 4.8 | 12.0 | 2.5 | 2.3 | 70 | 233.3 |
| 14 | AlKP$_{3.65}$ | 1:2.5:28 | 360 | 1 | 85.0 | 78.8 | 2.9 | 12.6 | 5.3 | 0.5 | 67 | ·67 |
| 15 | AlKP$_{3.65}$ | 1:3:28 | 390 | 1 | — | — | — | — | — | — | 74.8 | 74.8 |
| 16 | NiCaP$_{3.85}$ | 1:3:28 | 375 | 1 | 91.0 | 76.0 | 4.8 | 11.7 | 6.2 | 1.3 | 69.2 | 69.2 |
| 17 | NiCaP$_{3.85}$ | 1:4:28 | 360 | 0.5 | 95.8 | 71.2 | — | — | — | — | 68.2 | 136.4 |
| 18 | Zr$_2$KP$_{4.95}$ | 1:3:28 | 390 | 0.3 | 94.8 | 76.2 | 3.9 | 11.7 | 7.3 | 0.9 | 72.2 | 240.7 |
| 19 | Zr$_{0.5}$KP$_{3.3}$ | 1:2:28 | 390 | 0.3 | 90.8 | 82.9 | 3.0 | 9.9 | 3.4 | 0.8 | 75.3 | 251.0 |

EXAMPLE 18

The catalyst was prepared according to example 11, varying the atomic ratios of the elements so as to get a compound of the empirical formula:

$$Fe_{1.5}K_1Zr_2P_{4.95}O_z$$

The procedure was as in example 11, but the fed-in mixture consisted of isobutyric acid, air and water in molar ratios of 1:3:28. The reaction temperature amounted to 390° C. while the residence time was 0.3 seconds. Data and results have been recorded in Table I.

EXAMPLE 19

The catalyst was prepared as in example 12, by varying the molar ratios of the elements so as to get a compound of empirical formula:

$$Fe_{1.5}K_1Zr_{0.5}P_{3.3}O_z$$

The procedure was as in example 12, bringing the reaction temperature to 390° C. and the residence time to 0.3 seconds. Data and results have been recorded in Table I.

EXAMPLE 20

Example 19 was repeated, replacing potassium by cesium so as to get a compound of empirical formula:

$$Fe_{1.5}Cs_1Zr_{0.5}P_{3.3}O_z$$

Thereupon it was proceeded as in example 19 and were obtained results considerably better than those of example 19 itself, and even, if only slightly, better with respect to the catalysts containing only cesium, that is, lacking zirconium.

We claim:

1. Process for the production of methacrylic acid by an oxidative dehydrogenation, at between 340° and 440° C., of the corresponding saturated acid with oxygen in the gaseous phase, the process being characterized in that the catalyst consists of a compound of the empirical formula:

$$FeP_xMe_yMe'_tO_z$$

wherein Me represents at least one alkali or alkaline earth element, Me' represents zirconium, x is between 0.2 and 15, y is between 0.01 and 2, t is between 0.01 and 5 and z is such as to satisfy the valencies of the other elements.

* * * * *